United States Patent [19]

Gabbay

[11] 4,423,730

[45] Jan. 3, 1984

[54] ATRIOTOMY BUTTON AND IMPLANTATION DEVICE

[75] Inventor: Shlomo Gabbay, Hartsdale, N.Y.

[73] Assignee: Shelhigh Inc., Hartsdale, N.Y.

[21] Appl. No.: 353,343

[22] Filed: Mar. 1, 1982

[51] Int. Cl.³ .................... A61B 17/10; A61M 5/00
[52] U.S. Cl. .................... 128/334 R; 604/175
[58] Field of Search .............. 128/347, 330, 214 R, 128/334 C, 334 R, 1 R, 303 R, 305.3; 3/1.5; 24/19, 278; 604/49, 93, 4, 174, 175, 280, 283, 27, 164

[56] References Cited

U.S. PATENT DOCUMENTS

| | | | |
|---|---|---|---|
| 2,453,056 | 11/1948 | Zack | 128/334 C |
| 2,621,383 | 12/1952 | Tresidder et al. | 24/278 |
| 2,809,066 | 10/1957 | Curtis | 24/19 X |
| 3,048,177 | 8/1962 | Takaro | 128/334 C |
| 3,435,823 | 4/1969 | Edwards | 128/334 C |
| 3,540,451 | 11/1970 | Zeman | 604/283 X |
| 3,555,636 | 1/1971 | Turner | 24/278 |
| 3,643,649 | 2/1972 | Amato | 128/305.3 X |
| 3,991,743 | 11/1976 | Bucalo | 128/1 R |
| 4,033,349 | 7/1977 | Baehr | 128/1 R X |
| 4,214,586 | 7/1980 | Mericle | 128/334 R |
| 4,318,401 | 3/1982 | Zimmerman | 128/347 X |
| 4,329,987 | 5/1982 | Rogers et al. | 128/214 R |
| 4,366,819 | 1/1983 | Kaster | 128/334 C |
| 4,368,736 | 1/1983 | Kaster | 128/334 C |

OTHER PUBLICATIONS

Malette, William, et al., *An Improved Peritoneal Access Button for Dialysis in Chronic Renal Failure*, Surgery, vol. 55, No. 4. Apr. 1964, pp. 500–504.

*Primary Examiner*—C. Fred Rosenbaum
*Assistant Examiner*—Michelle N. Lester
*Attorney, Agent, or Firm*—Jordan B. Bierman; Linda Bierman; C. Cornell Remsen, Jr.

[57] ABSTRACT

A device and procedure are provided which enable the attachment of a hollow cylindrical atriotomy button to, for example, the atrial appendage. The inventive device, which carries on its end the inner portion of an atriotomy button, is inserted through an incision in the hollow organ. When the device is triggered, the outer portion of the atriotomy button is forced over the inner portion. Sharp points, which are formed on the edge of the inner section, grasp and guide the walls of the incision during the operation of the device so that the walls are effectively clamped between the two button portions. After the button is in place, a cannula can be inserted into the heart through the access button or attached to the outer surface of the outer button portion.

5 Claims, 9 Drawing Figures

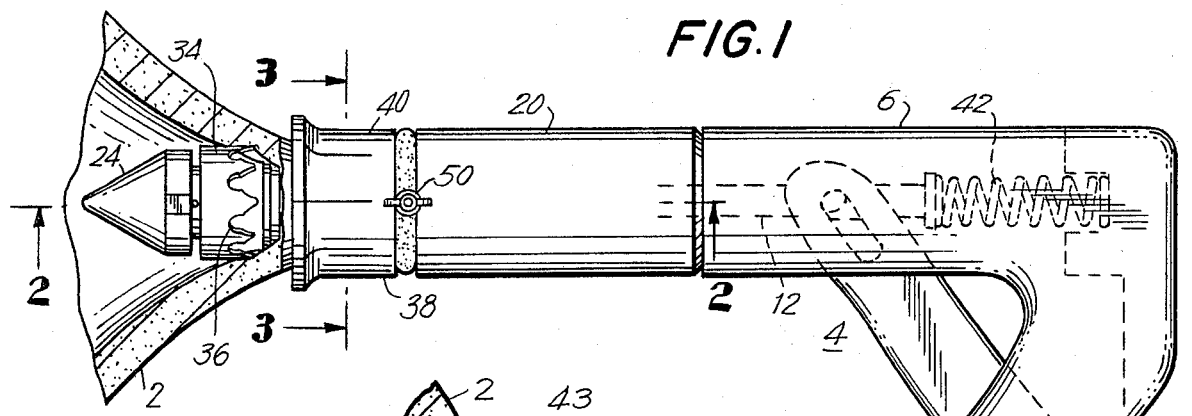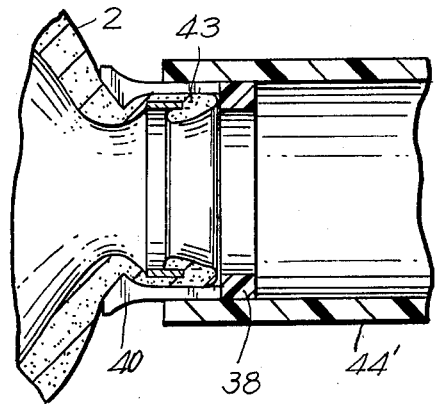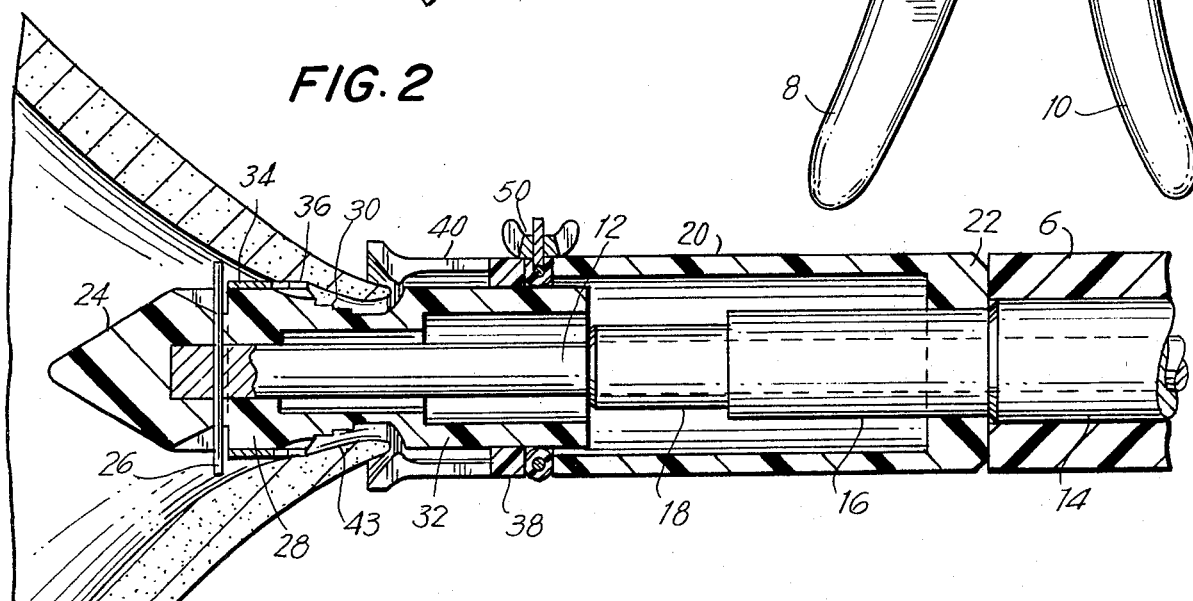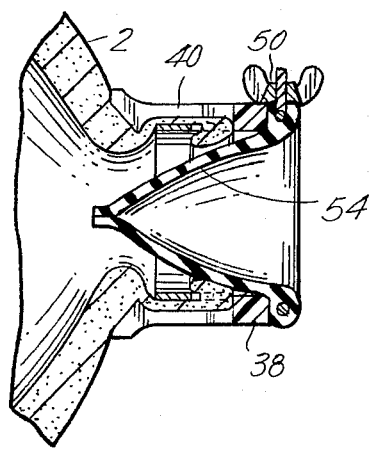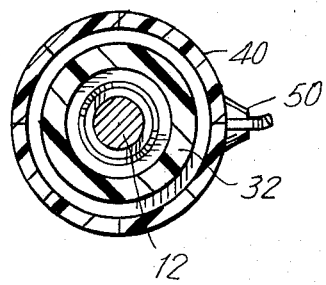

ATRIOTOMY BUTTON AND IMPLANTATION DEVICE

The procedure known as venous cannulation involves the insertion of one or two tubes (cannula) in the right atrium of the heart of provide a cardiopulmonary by-pass to direct blood to the heart-lung machine. The procedure is necessary and "standard", for example, in open-heart surgery to permit corrective operation on the heart itself.

Up to the present time such cannulation is usually effected by clamping the right artrial appendage and placing a purse-string suture thereon. The top of the appendage is excised and the connecting tissue cut. While the walls of the appendage are held by the surgeon and his assistant, the clamp is opened by the assistant and the surgeon inserts the cannula. After the latter is positioned, the tourniquet is tightened and the tourniquet and cannula are tied together. If a second cannula is necessary, a second purse-string suture is placed in a portion of the artrial wall and a similar procedure is followed.

Clearly the procedure described is time consuming and sometimes requires more than one assistant to help introduce the cannula. Moreover the surgical field, already overloaded with rubbers and clamps, interferes with the surgical procedure. A distinct and sometimes fatal disadvantage lies in the fact that once the cannula is removed at the end of the procedure, if recannulation is required as the result of an emergency such as sudden heart failure it can be disastrous for the patient. It is to be kept in mind that many cannulations are done by young and relatively inexperienced residents and the entire procedure can be messy and traumatic to the patient's atrium.

It is an object of the present invention to provide a device which together with a special instrument therefor will result in a cannulation procedure which eliminates the use of sutures, drastically reduces the time required and permits a ready and simple recannulation.

More specifically, my invention makes use of the implantation of an atriotomy button in the right atrial appendage or wall of the heart, the said button having a central opening through which the cannula can be inserted force fit into the heart. Alternatively the cannula may be attached to the circumference of the button. When the cannula is to be removed, it is merely pulled out (or off) and a plug inserted in the button. If an emergency arises and a cannula is again required, the plug is removed and the cannula reinserted or reconnected. If all is eventually satisfactory and the surgeon is ready to close the chest, the atrium will be tied below the button and the latter merely cut off.

While various means may be provided for implantation of my atriotomy button, I have also provided according to this invention a form of instrument or tool to facilitate such implantation.

Other objects and advantages of the invention will become apparent from the following description thereof read with reference to the attached drawings in which FIG. 1 is a plan view showing an appropriate tool inserting an atriotomy button of the present invention into an incised right atrial appendage;

FIG. 2 is an enlarged longitudinal cross-sectional view of the end of the tool supporting the atriotomy button taken along the line 2—2 of FIG. 1;

FIG. 3 is an enlarged cross-sectional view taken along the line 3—3 of FIG. 1;

FIG. 8 is a cross-sectional view of a modified form of atriotomy button; and

FIG. 9 is a cross-sectional view similar to FIG. 8 showing a further alternative arrangement.

Figure 4:
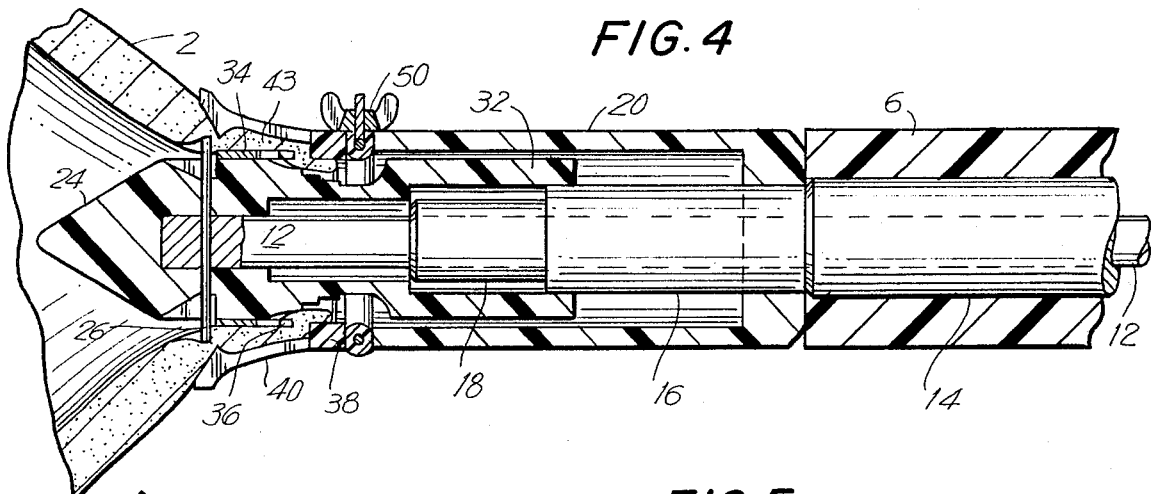
FIG. 4 is a longitudinal cross-sectional view similar to FIG. 2 in which the tool has been actuated to initiate clamping of the atriotomy button.

While the invention is not necessarily so limited, it has been designed for and will be described in connection with the insertion of a cannula in the right atrial appendage 2 of the human heart. The tool 4 for inserting and attaching the atriotomy button of the present invention (as described in more detail hereinafter) may take the form of a cylindrical casing 6, having an extending stationary handle or grip 8 to which is pivoted a movable handle 10 suitably connected to a longitudinally movable rod 12 centrally supported in a cylindrical sheath 14 mounted within and projecting from casing 6. That portion of sheath 14 projecting from casing 6 has a first extension 16 of smaller outer diameter and a second extension 18 of still smaller outer diameter.

A cylindrical collar 20, open at one end, is closed at its other end 22 which has a central opening slidably fitting about the first extension 16 of sheath 14.

Casing 6 of tool 4, being a permanent portion of the tool, may be made of metal or plastic. Collar 20, on the other hand, can be considered to be a disposable item formed of plastic.

The tool 4 as aforedescribed is adapted to insert the atriotomy button of this invention in separated form within and about the incised opening in atrial appendage 2, and for this purpose is provided with a smooth plastic piercing end or nose piece 24 supported at the extremity of rod 12 by a friction-fit yieldable pin 26. Nose piece 24, moreover, is formed with a first cylindrical section 28 formed just rearwardly of pin 26, followed by an intermediate hollow section 30 of gradually decreasing and then abruptly increasing diameter, ending with an enlarged hollow cylindrical section 32.

The atriotomy button itself is formed of two parts, a crowned flesh-engaging metallic ring 34 having a plurality of rearwardly extending sharp points 36, which is slid in friction fit over the cylindrical section 28 of nose piece 24, and a matching collar 38 supported on cylindrical section 32 and having a plurality of forwardly positioned flexible extensions 40. Collar 38 and extensions 40 are preferably formed of plastic material.

The initial assembly of the tool together with the atriotomy button will first be described. As seen particularly in FIGS. 1 and 2, in the normal position rod 12 will be pushed forward under the action of spring 42. Cylindrical collar 20 will be slipped over sheath extension 16. Collar 38 with forwardly extending flexible sections 40 will be placed over cylindrical section 32 of end piece 24 with a slight frictional fit. At the other end of the end piece, ring 34 will be slipped over the first cylindrical portion 28 with points 36 facing flexible sections 40 of collar 38. Wire pin 26 extending through matching holes in end piece 24 and rod 12 prevents ring 34 from slipping off the tip of end piece 24.

Figure 5:
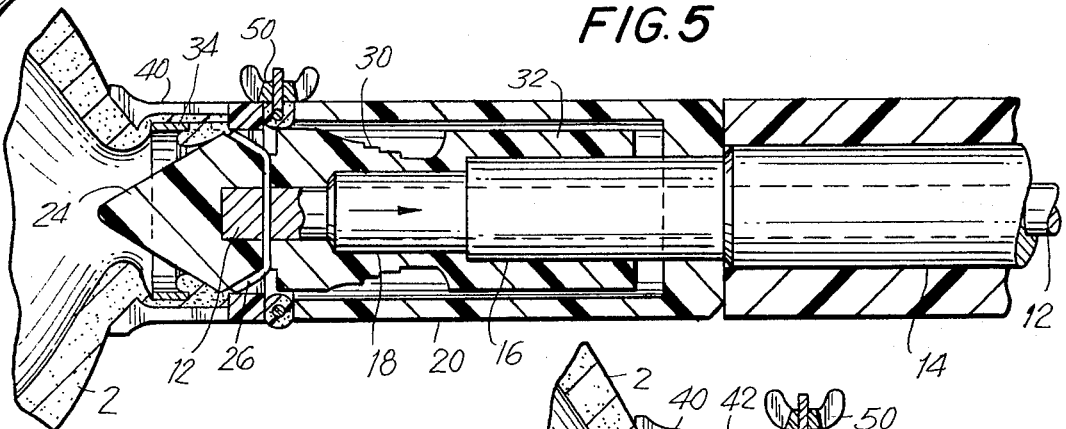
FIG. 5 is a further longitudinal cross-sectional view showing the atriotomy button about to be fully clamped about the atrial appendage.
Figure 6:
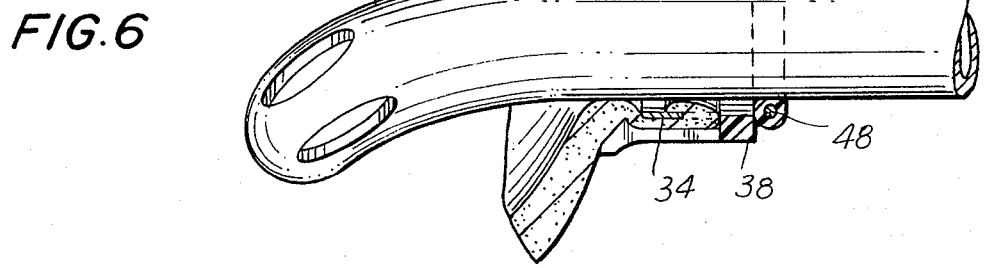
FIG. 6 is a similar cross-sectional view showing the atriotomy button supporting a cannula, with the tool completely withdrawn.

To perform the cannulation, the tip of the atrial appendage is excised and while an assistant is holding the edges the tool is introduced into the atrium to an extent sufficient to move end piece 24 and ring 34 within the cavity with the inner portion of flexible section 40 of collar 38 contacting the outside of the tip of the appendage. The squeezing together of handle 8 and 10 of the tool against the action of spring 42 will cause relative longitudinal movement between ring 34 and collar 38 effectively to pull ring 34 with its sharp parts 36 engaging the inner wall 43 of atrial appendage 2 within flexible sections 40 with the edges of the incision being compressed between them (FIG. 4), rearward movement of collar 38 being prevented by its abutment against cylindrical collar 20 which in turn abuts the end of casing 6. Movement of rod 12 brings the parts together as shown in FIG. 5. It will be seen that in this final position the hollow cylindrical section 32 of nose piece 24 has slid over section 16 of sheath 14 while the inner hollow portion of intermediate section 30 now surrounds the small section 18 of sheath 14. Nose piece 24 thus fits snugly within cylindrical collar 20. Upon further movement, the wire pin 26 now bends so that the nose piece 24 can be fully withdrawn through ring 34 and collar 38, and carrying collar 20 with it leaves a unitary button with a central opening attached to wall 43 of atrial appendage 2. This button can immediately be closed by the surgeon's thumb and then either stopped by a suitable plug, or cannulation can be performed immediately, as indicated in FIG. 6 showing a cannula 44 extending into the atrium and friction fit in the atriotomy button formed of parts 34 and 38.

Generally the atriotomy button and inserted cannula will be chosen of such size that the outer surface of them will form a tight fit with the inner diameter of the ring 34, so that there is no leakage between the cannula and the button. However as further assurance against leakage, the end of collar 38 may have adhesively attached thereto a face of a soft rubber collar 46. Collar 46 may contain flexible wire 48 which can be tightened in a known manner as by wing nut 50, all as more particularly shown in FIG. 6.

Figure 7:
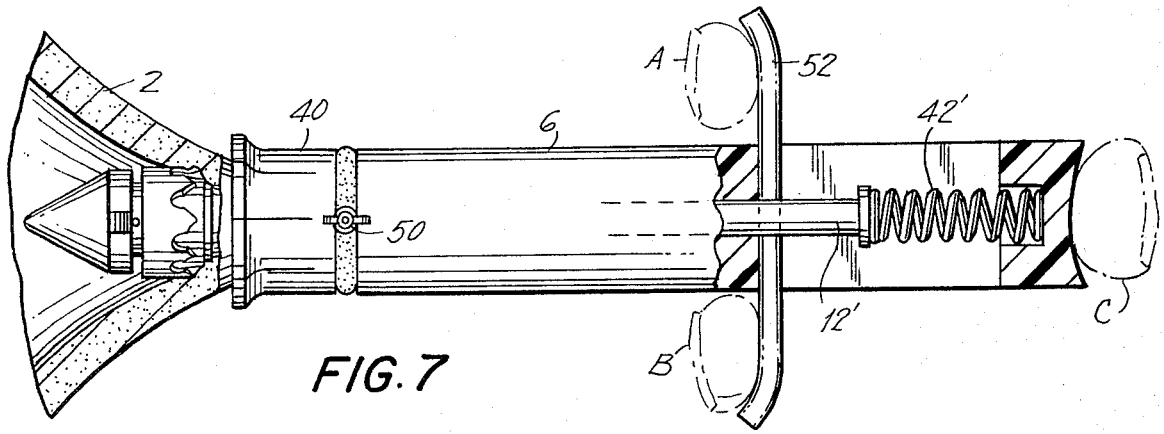
FIG. 7 is a plan view similar to FIG. 1 illustrating a modified form of tool.

The rod for pulling the button elements together about the atrial appendage can be actuated by means other than the tool shown in FIGS. 1-5. An alternative mechanism is illustrated in FIG. 7 in which rod 12' is formed with a transverse grip 52 slidable in a slot (not shown) in casing 6', against the action of spring 42'. Operation of the tool to insert and subsequently close the atriotomy button is then a very simple procedure, the tool being actuated as by fingers A, B, and C. In the form of invention shown in FIG. 7, I have dispensed with the cylindrical collar 20 of FIGS. 1-5.

Collar 38 in addition to being formed with soft compressible collar 46, may also be provided with an inwardly extending flap valve 54, as shown in FIG. 8. Such valve may be formed of any soft flexible material which will fold together under pressure to prevent leakage. Obviously it will readily open upon insertion of the cannula, as in FIG. 6. While the valve has been illustrated as forming a part of a soft compressible outer collar, it may be attached directly to the collar 38 and the soft collar disposed of.

FIG. 9 illustrates a variation of my invention which can be important in certain instances. Here cannula 44' is of sufficient internal diameter that it can be force fit over the outer surface of collar 38. By reason of such an arrangement, the danger of possible occlusion of the cannula's orifice by the atrial walls is avoided. Moreover, insertion of a cannula into the heart can be traumatic; it may also cause arrhythmias and other problems. These will not occur when a cannula is connected as shown.

My invention as above described constitutes the best modes thereof as presently conceived. It contemplates, however, that changes and improvements will occur to those skilled in the art. While I have described ring 34 as being of metal and engaging collar 38 with flexible sections 40 as being formed from a plastic material, obviously metal such as stainless steel may well serve the purpose. The manner of temporarily holding ring 34 on the end piece 24 of the tool by means of yieldable wire pin 26 could be accomplished by other equivalent releasable means. Activation and support of rod 12 may well be effected by equivalent mechanical means other than that specifically described.

Thus, in addition to the examples given, it is my intention that my invention not be limited thereto, but only as may be required by the claims which follow.

I claim:

1. Atriotomy button comprising a metal ring having a plurality of forwardly longitudinally extending circumferentially spaced pointed extensions, and a collar having a plurality of longitudinally extending circumferentially spaced flexible extensions radially spaced outwardly from and directed toward the extensions on said ring, the inner diameter of that portion of the collar extending toward the metal ring being sufficiently larger than the outer diameter of the pointed extensions on said ring so that a substance grasped by said pointed extensions may be firmly held between said ring and collar when the ring is moved into and within the said collar.

2. Atriotomy button according to claim 1, in combination with a soft compressible collar attached to the first collar on the side opposite said flexible extensions, and means for inwardly compressing said compressible collar.

3. Cannulation device comprising a metallic ring section having sharp longitudinally extending projections, a collar section having circumferentially spaced flexible extensions having an internal diameter greater than the external diameter of said ring, means mounting said collar spaced from and coaxially with said ring with the flexible extensions of the collar facing the sharp projections from said ring, means detachably connected to said ring section for moving the same through an incision of a hollow organ to be cannulated with the projections of said ring contacting the inner walls of the incision, said means including further means pulling said ring and the contacted walls of the incision within the flexible extensions on said collar, whereby the said walls are clamped in a hollow atriotomy button formed by the outer surface of said ring and the inner surface of said flexible extension.

4. Cannulation device comprising a tool having a casing supporting a hollow shaft protruding therefrom, said shaft having two protruding sections of increasingly small external diameter, a hollow cylindrical member surrounding the protruding portions of said shaft, said member having an internal diameter substantially greater than that portion of the shaft which it surrounds and having a partially closed section at one end having an internal diameter substantially equal to the external diameter of the larger protruding section of the shaft, the other end of said member extending substantially beyond the end of said shaft, a rod slidably mounted within said hollow shaft, said rod being of such length that in its extended position its end projects substantially beyond the open end of said cylindrical member, a longitudinally extending nose piece adapted to be attached to the projecting end of said rod, said nose piece having a first end section on the end of the rod having an organ-penetrating section followed rearwardly by a first cylindrical portion having an external diameter less than the internal diameter of said cylindrical member, an intermediate portion of gradually decreasing then abruptly increasing outer diameter, and an internal diameter substantially equal to the outer diameter of the smaller protruding section of said shaft, and a second cylindrical portion having an external diameter substantially equal to the external diameter of said first cylindrical portion and an internal diameter substantially equal to the external diameter of the larger protruding section of said shaft, a ring mounted on the first cylindrical portion of said nose piece, said ring having sharp projections extending longitudinally rearwardly therefrom, detachable means preventing forward longitudinal movement of said ring on said first cylindrical portion, and a collar slidably mounted on the second cylindrical portion of said nose piece in abutting relationship with the open end of said hollow cylindrical member, said collar having circumferentially spaced forwardly extending flexible projections having an internal diameter greater than the external diameter of said ring, whereby when the nose piece of said tool is moved behind the incised wall of a hollow organ and then withdrawn, the projections on said ring pull the edges of the incision with the flexible projections of said collar with the end of the smaller section of said shaft abutting the inside of said nose piece, whereby further rearward movement of said rod actuates said detachable means to permit complete withdrawal of the tool, leaving the wall of the hollow organ clamped within the periphery of a hollow atriotomy button formed by the force fit of said ring with said flexible projections.

5. Cannulation device according to claim 4, in which the end of said rod within said nose piece has an opening therethrough, and said detachable means comprises a bendable wire mounted in said opening.

* * * * *